US00PP12531P2

(12) United States Plant Patent
Machen, Jr.

(10) Patent No.: US PP12,531 P2
(45) Date of Patent: Apr. 9, 2002

(54) HOSTA PLANT NAMED 'LIBERTY'

(76) Inventor: John Lee Machen, Jr., HC75 Box 7965, Mobjack, VA (US) 23056

( * ) Notice: Subject to any disclaimer, the term of this patent is extended or adjusted under 35 U.S.C. 154(b) by 0 days.

(21) Appl. No.: 09/442,325

(22) Filed: Nov. 17, 1999

(51) Int. Cl.[7] ..... A01H 5/00

(52) U.S. Cl. ..... Plt./353
(58) Field of Search ..... Plt./353

*Primary Examiner*—Bruce R. Campell
*Assistant Examiner*—June Hwu

(57) ABSTRACT

A distinct cultivar of Hosta named 'Liberty' particularly characterized by its wide yellow to cream colored leaf margins, its large upright growth habit, its thick and gently undulating leaves, and pale-lavender flowers in mid summer.

3 Drawing Sheets

BACKGROUND OF THE INVENTION

Figure 1:
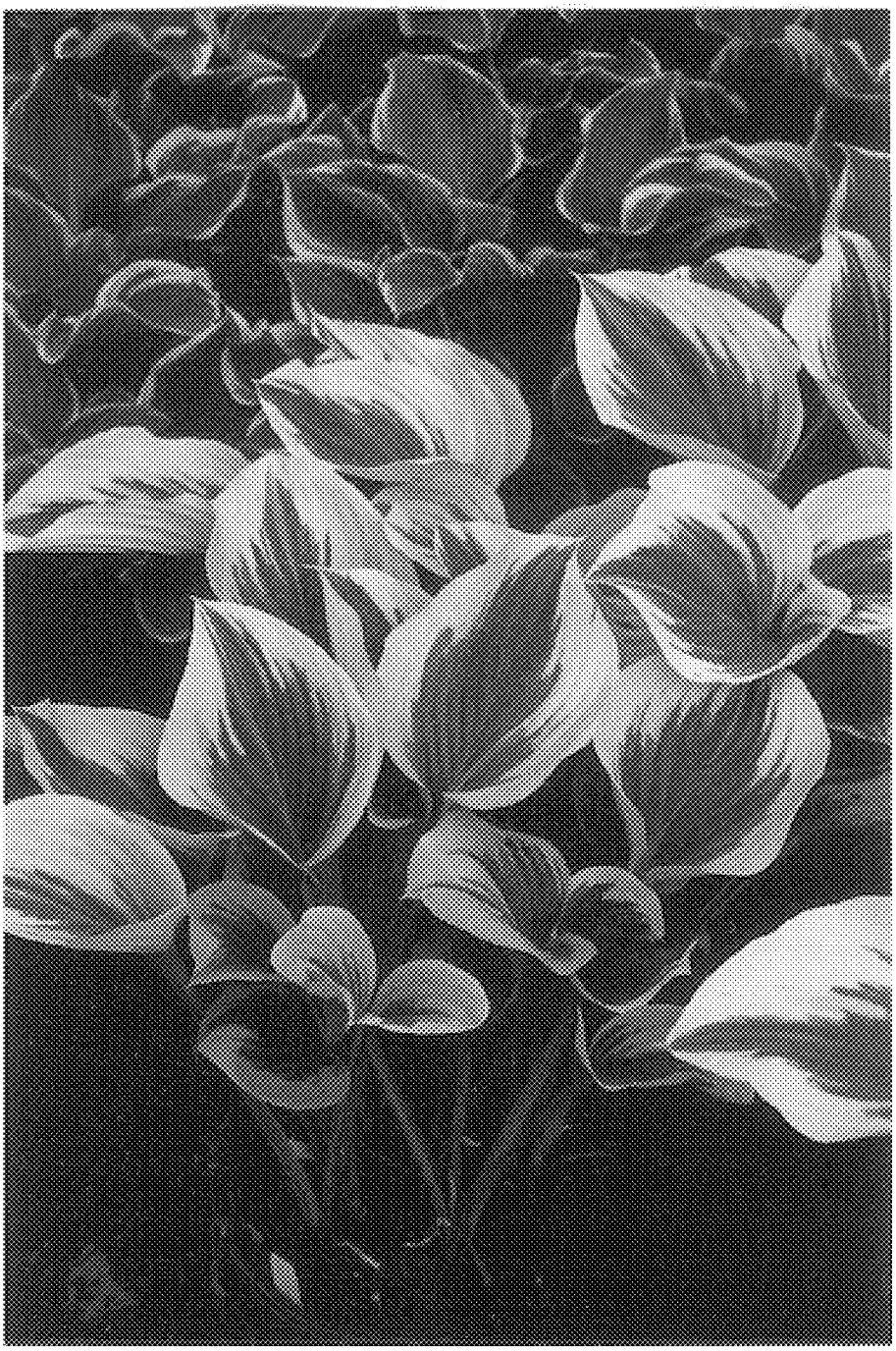

The present invention, *Hosta fluctuans* 'Liberty', relates to a new and distinct cultivar of Hosta. This unique sport of Hosta 'Sagae' (unpatented), hereinafter referred to as 'Liberty', has a distinctive broad yellow leaf margin that is much wider than that of its parent.

I have grown Hosta under large scale production for 20 years and during that period I have taken an interest in identifying and isolating sports and mutations that were unique and had the potential for market value. I have selected, registered and introduced three sports that have become significant internationally. My experience with the Genus Hosta allows me to be confident that 'Liberty' is unique and unlike any existing cultivar known to me.

The striking margins on 'Liberty' were first noticed while growing in a block of Hosta 'Sagae' in my nursery in Mobjack, Va. in the summer of 1996. I divided the original clump into 5 divisions in the winter of 1997. Those divisions matured and the division with the broadest variegated margin was selected as 'Liberty'. A division of the new cultivar was sent for propagating my micropropagation in 1998 in Waseca, Minn. and the plants derived from culture have the identical wide variegation as the original plant. The characteristics of this new cultivar have therefore been determined to be stable and are reproduced true to type in successive generations.

The new Hosta has distinctive broad yellow irregular margins on its leaves. The margin is much wider than of its parent, Hosta 'Sagae'. The variegation of 'Liberty' comprises almost a third of the leaf area; giving the whole plant a much brighter appearance. The growth habit, foliage coloration and flowers of 'Liberty' are similar to that of Hosta 'Sagae'.

SUMMARY OF THE INVENTION

The following traits have been repeatedly observed and represent the characteristics of the new cultivar, 'Liberty'. These attributes in combination distinguish 'Liberty' as a new and distinct cultivar of Hosta.

1. Leaf margins that comprise about one third of the leaf area that emerge a yellow color and lighten to a cream color as the leaf ages. The margins of Hosta 'Sagae' are much narrower. The leaf centers are a glaucous green color. An irregular, lighter glaucous green area exists between the leaf center and margin.

2. Upright vase-shaped growth habit.

3. Leaves emerge twisted but become gently undulated as they mature.

4. Pale lavender flowers are present above the foliage on arching scapes in mid summer.

BRIEF DESCRPTION OF THE DRAWING

In FIG. 1, three three-gallon containers of 'Liberty' are shown in the foreground. The distinctive leaf margins can be compared to that of the parent plant Hosta 'Sagae' that is shown in the background.

Figure 2:
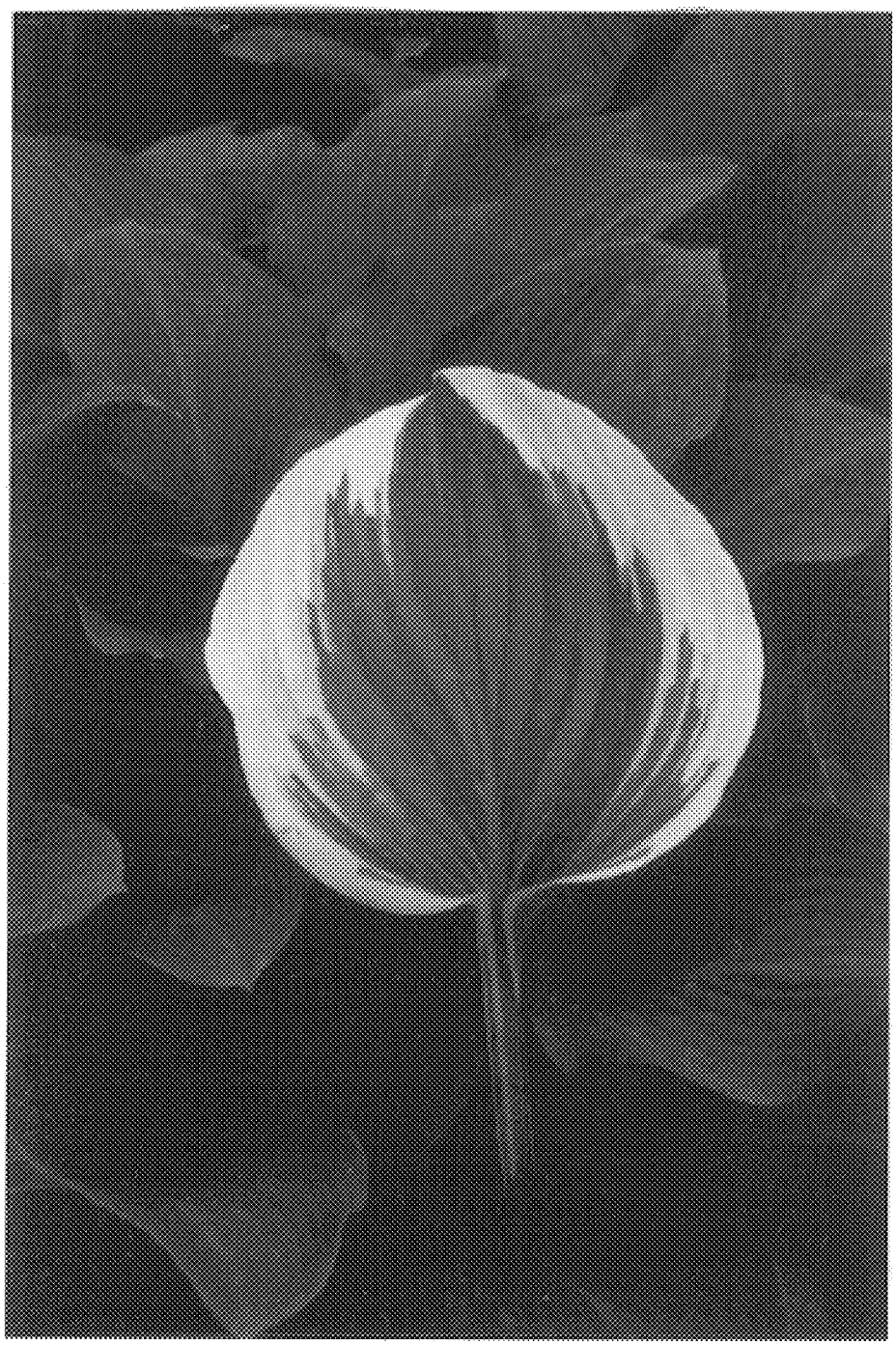

FIG. 2 is of a single leaf of 'Liberty' that is placed on a plant of 'Krossa Regal' (unpatented) as a background. The margin color is of a mature leaf and the transitional color and pattern between the center and margin can be observed. The upright habit of 'Liberty' is apparent in FIG. 3.

Figure 3:
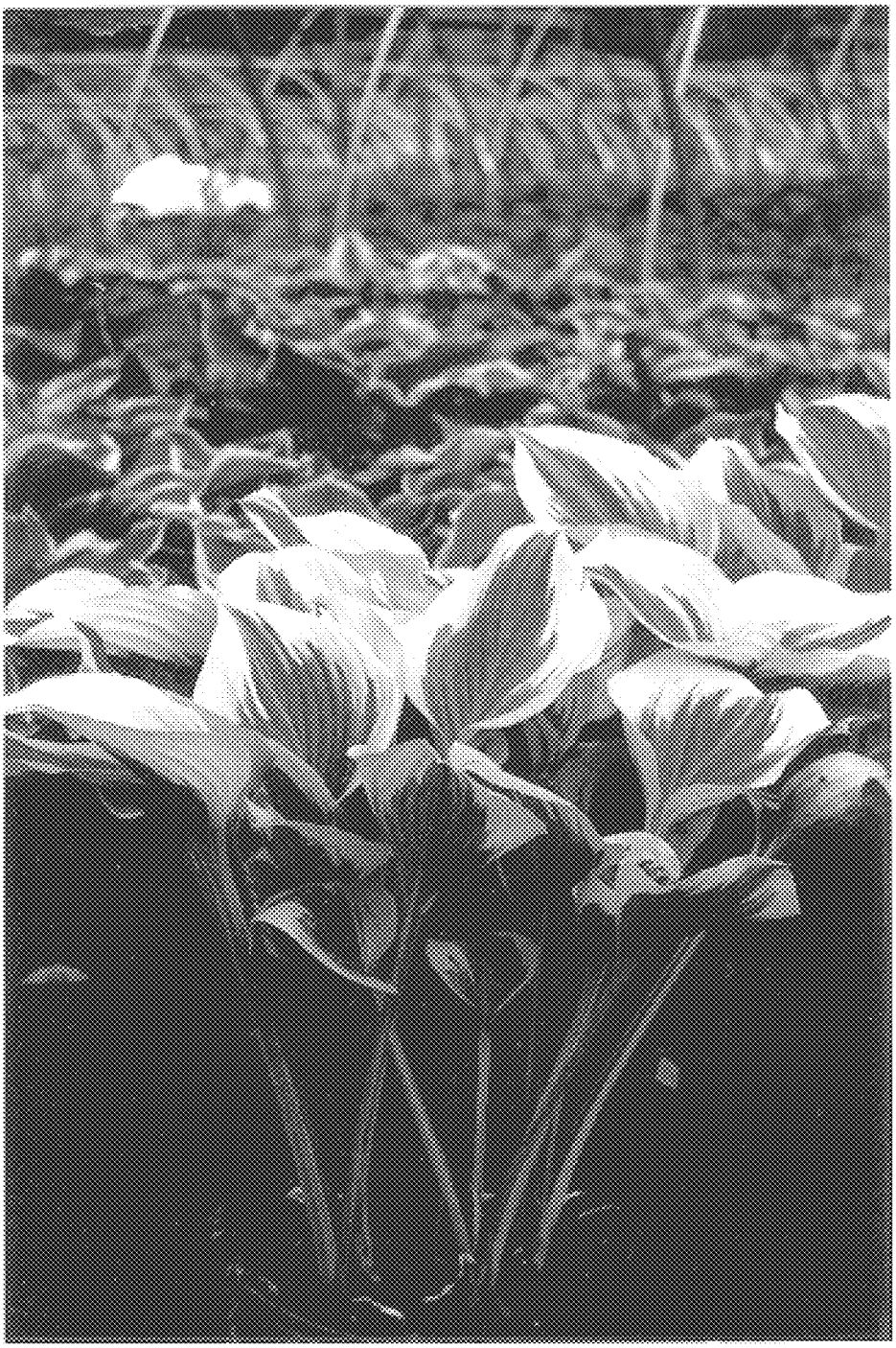

FIG. 3 is of the same three 'Liberty' plants shown in FIG. 1 with a block of 'Sagae' plants in the background. All the photographs are as true as can be reasonably obtained with conventional photography.

BOTANICAL DESCRIPTION OF THE PLANT

The following is a description of 3 year old plants of the new cultivar as grown outdoors under 54% shade cloth in a three gallon container in my nursery in Mobjack, Va. Phenotypic differences may be observed with variations in environmental, climatic, and cultural conditions. The new cultivar has not been tested under all possible conditions. All color references are made with The Royal Horticultural Society Colour Chart except where general terms of ordinary dictionary significance are used.

Botanical classification: *Hosta fluctuans* 'Liberty'.
Parentage: Naturally occurring mutation of Hosta 'Sagae' (syn. *Hosta fluctuans*, 'Variegated').
General description:
- *Blooming period.*—Midseason (relative to Hostas). Mid summer in Virginia.
- *Plant habit.*—Upright, vase-shaped mound.
- *Height and spread.*—60 cm in height, up to 60 cm in width when mature in 3 to 4 years.
- *Growth rate.*—Relatively slow to make new divisions.
- *Hardiness.*—Zone 3–8.
- *Type.*—Herbaceous perennial.
- *Root system.*—Branching, fleshy roots.

*Propagation.*—Division and tissue culture.

*Culture.*—Moist soils, light shade to full shade.

*Disease resistance.*—Heavy leaf substance confers slug resistance. No known resistance or susceptibility to other diseases known to Hosta has been observed.

Foliage description:

*Leaf shape.*—Broadly wedge-shaped (ovate), simple. Emerging twisted and becoming gently undulated as the leaf matures. Apex is cuspidate. Base is cordate.

*Leaf arrangement.*—Basal; radiate spirally from base.

*Leaf margin.*—Entire.

*Leaf size.*—28 cm in length, 25 cm in width.

*Leaf texture.*—Glacuous, good substance.

*Leaf venation pattern.*—12 pairs of veins. Campylodrome; veins curve outwards as the leaf widens and then curve inwards as the leaf narrows towards the tip. Veins appear impressed on the upper surface and prominent on the lower surface.

*Leaf orientation.*—Held horizontal on upright petioles.

*Leaf color and variegation pattern.*—Centers (upper, lower surface); glaucous green (137A,137B) with an irregular transitional area that is a lighter green (146D, 146D).

*Margins* (*upper, lower surface*).—4 to 5 cm in width, comprising about one third of the leaf area, irregular in pattern, yellow green (151A, 151A) when the leaf emerges and changing to a yellow color in mid season (4B, 4B) and changing to a cream color as the leaf matures (11C, 11C).

*Petiole size.*—25–50 cm in length, 1.5 cm in width.

*Petiole type.*—Sulcate.

*Petiole color.*—137A streaked with 146D, glaucous.

Flower description:

*Scapes.*—90–100 cm in height, solid, Sound, 137 B in color, arching, small leafy bracts, arise from leaf axils, 3–4 per scape.

*Leaf bracts.*—3 to 4 per scape, centers are 137A in color with margins 4B in color, 1.0–2.5 cm in length and 0.5–1.0 cm in width, ovate, surface is glaucous.

*Floral bracts.*—1 per flower, ovate in shape, surface is glaucous, 157C in color, 0.5–0.75 cm in width and 0.75–1.5 cm in length.

*Pedicels.*—1.5 mm in diameter, 3 mm in length, 137D in color.

*Flower arrangement.*—Raceme of numerous (30–40) single flowers comprised of six tepals.

*Flower shape.*—Funnel-shaped.

*Flower size.*—5.5 cm in length, 2.5 cm in width.

*Flower color* (*tepals*).—Pale-lavender (85 D) with a thin, vertical, white (155C) stripe down the interior of each tepal.

*Reproduction organs.*—Stamens; 6, 8D in color, 5–6 cm in length (equal or slightly shorter than perianth). Pistils: 6–7 cm in length, 155C in color, 3-lobed stigma, compound ovary of 3 locules.

*Fruit/seed.*—Capsule, 3 parted, 137 D in color, 6 cm in length and 0.6 cm in width. Seeds are 3.0 mm in length, 1.5 mm in width, ovate and nearly flat, 200A in color, 30–40 in number.

I claim:

1. A new and distinct cultivar of Hosta plant named 'Liberty' substantially as herein illustrated and described.

* * * * *